(12) United States Patent
Dubey et al.

(10) Patent No.: US 7,793,535 B2
(45) Date of Patent: Sep. 14, 2010

(54) DEVICES AND METHODS TO SIMULATE AN OCULAR ENVIRONMENT

(75) Inventors: Dharmesh K. Dubey, Jacksonville, FL (US); Lauren May, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 153 days.

(21) Appl. No.: 11/923,680

(22) Filed: Oct. 25, 2007

(65) Prior Publication Data

US 2008/0100795 A1    May 1, 2008

Related U.S. Application Data

(60) Provisional application No. 60/855,433, filed on Oct. 31, 2006.

(51) Int. Cl.
*G01N 15/08* (2006.01)
*G01N 13/04* (2006.01)

(52) U.S. Cl. .......................... 73/38; 73/64.47

(58) Field of Classification Search .......... 73/38, 73/64.47
See application file for complete search history.

(56) References Cited

U.S. PATENT DOCUMENTS

| | | | |
|---|---|---|---|
| 4,782,946 A * | 11/1988 | Pollak | 206/223 |
| 4,955,580 A * | 9/1990 | Seden et al. | 249/82 |
| 5,490,415 A * | 2/1996 | Mak et al. | 73/64.47 |
| 5,710,302 A | 1/1998 | Kunzler | |
| 5,760,100 A | 6/1998 | Nicolson | |
| 5,776,999 A | 7/1998 | Nicolson et al. | |
| 5,789,461 A | 8/1998 | Nicolson | |
| 5,817,924 A | 10/1998 | Tuomela et al. | |
| 5,849,811 A | 12/1998 | Nicolson | |
| 5,882,698 A * | 3/1999 | Su et al. | 425/215 |
| 5,965,631 A | 10/1999 | Nicolson | |
| 5,998,498 A | 12/1999 | Vanderlaan | |
| 6,087,415 A | 7/2000 | Vanderlaan | |
| 6,450,014 B1 * | 9/2002 | Boris | 73/64.47 |
| 6,909,503 B2 * | 6/2005 | Baske et al. | 356/246 |
| 6,981,403 B2 * | 1/2006 | Ascheman et al. | 73/38 |
| 2003/0024829 A1 * | 2/2003 | Matsuzawa et al. | 206/5.1 |
| 2004/0096477 A1 | 5/2004 | Chauhan et al. | |
| 2008/0190221 A1 * | 8/2008 | Pegram et al. | 73/864.84 |

FOREIGN PATENT DOCUMENTS

| | | |
|---|---|---|
| EP | 406161 A2 | 1/1991 |
| EP | 0830865 | 3/1998 |
| JP | 2000016905 A | 1/2000 |
| WO | WO 9421698 A1 | 9/1994 |

OTHER PUBLICATIONS

R.Uchida, T. Sato, H. Tanigawa, K. Uno. "Azulene incorporation and release by hydrogel containing methacrylamide propyltrimenthylammonium chloride, and its application to soft contact lens." Journal of Controlled Release 92 (2003) pp. 259-264.*

D. R. Morrison and H. F. Edelhauser. "Permeability of hydrophilic contact lenses." Investigative Ophthalmology. vol. 11, No. 1, Jan. 1972. pp. 58-63.*

Karlgard, C.C.S., "In vitro uptake and release studies of ocular pharmaceutical agents by silicon-containing and p-HEMA hydrogel contact lens materials", International Journal of Pharmaceutics, Amsterdam, NL, vol. 257, No. 1-2, May 12, 2003.

* cited by examiner

*Primary Examiner*—Lisa M Caputo
*Assistant Examiner*—Punam Roy

(57) ABSTRACT

Methods and devices used to simulate the use of an ophthalmic lens contained in an ocular environment are disclosed herein.

10 Claims, 7 Drawing Sheets

DEVICES AND METHODS TO SIMULATE AN OCULAR ENVIRONMENT

RELATED APPLICATION

This application is a non-provisional filing of a provisional application, U.S. Ser. No. 60/855,433, filed on Oct. 31, 2006.

FIELD OF THE INVENTION

This invention related to devices and methods simulate an ocular environment to enable the testing of ophthalmic lens.

BACKGROUND

Most diseases of the eye are treated with topical ophthalmic solutions containing pharmaceutical agents. It has been postulated that delivery and efficacy of these agents would be greatly increased if the agents were incorporated in ophthalmic lenses and those lenses were used as drug delivery devices. These agents may be added to the ophthalmic lenses by a variety of methods including soaking the agent into a formed lens, adding the agent to the formulation of the lens prior to its formation and the like. Others have postulated methods of testing the uptake and discharge rates of such pharmaceutical agents to and from the ophthalmic lenses. These methods include placing ophthalmic lenses in solutions and monitoring the concentration of the pharmaceutical agent over time. Even though these methods work, due to the volume of solution used in the test, the conditions do not mimic the conditions that an ophthalmic lens is exposed to when inserted into an ocular environment.

In an ocular environment, very small volumes of tear fluid pass over the lens during its use. Therefore it would be beneficial if one could mimic those conditions to test the performance of ophthalmic lenses. This need is met by the following invention

DETAILED DESCRIPTION OF THE INVENTION

This invention includes an apparatus for testing an ophthalmic lens comprising a male mold and a female mold,
   wherein said male mold comprises a convex testing surface, an outer male surface, male seating ridge extending from the perimeter of the convex testing surface, and an aperture extending from said outer male surface to said convex testing surface,
   wherein said female mold comprises an outer female surface a concave testing surface, female seating ridge extending from the perimeter of the concave testing surface, and an aperture extending from said concave testing surface to said outer female surface,
   wherein when the male mold and the female mold are mated, the male seating ridge sits on the female seating ridge and creates a testing area between the male convex testing surface and the female concave testing surface.

An embodiment of the invention is illustrated in the following figures.

Figure 1:
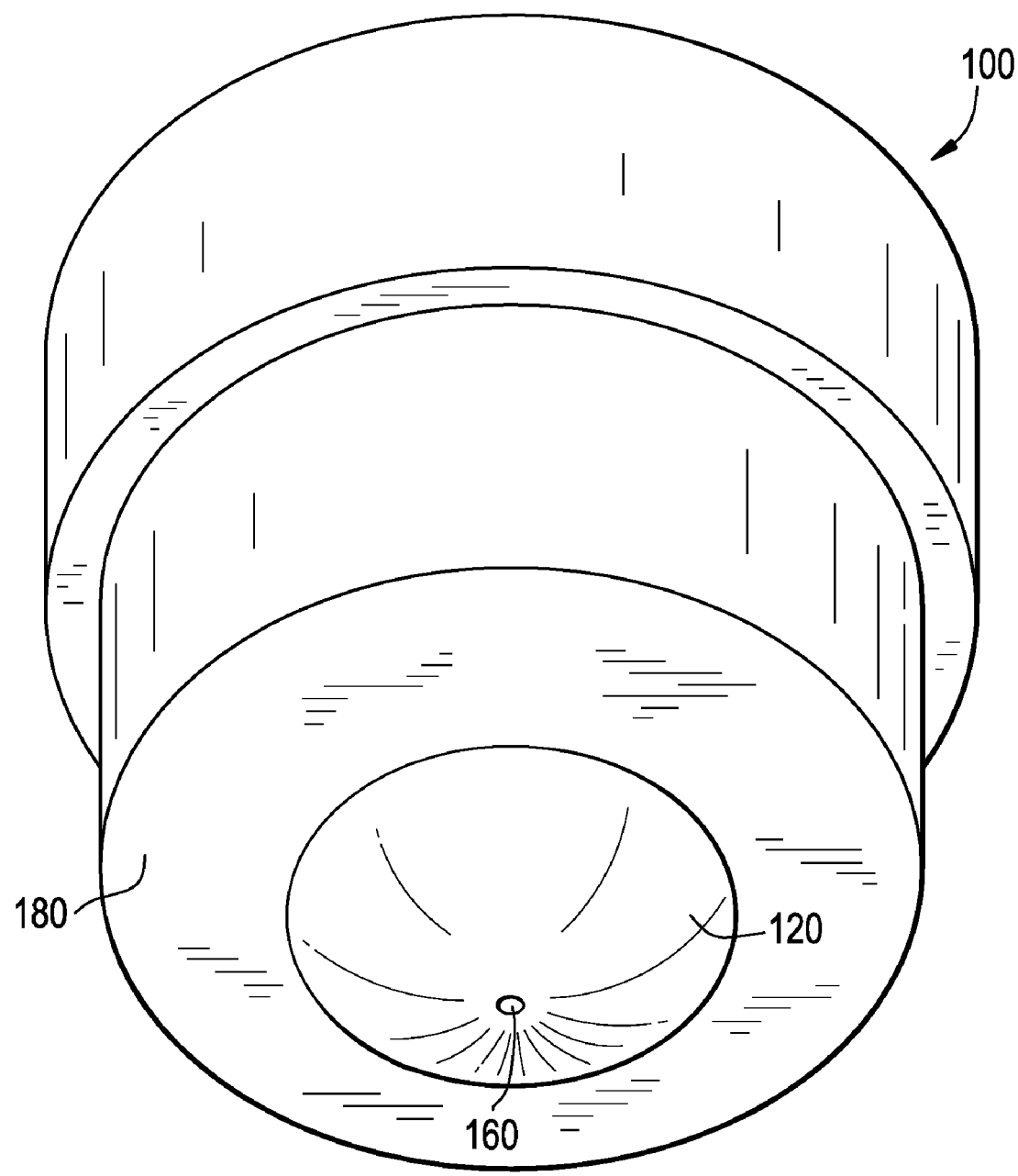
FIG. 1 illustrates a perspective drawing of a male mold.
Figure 2:
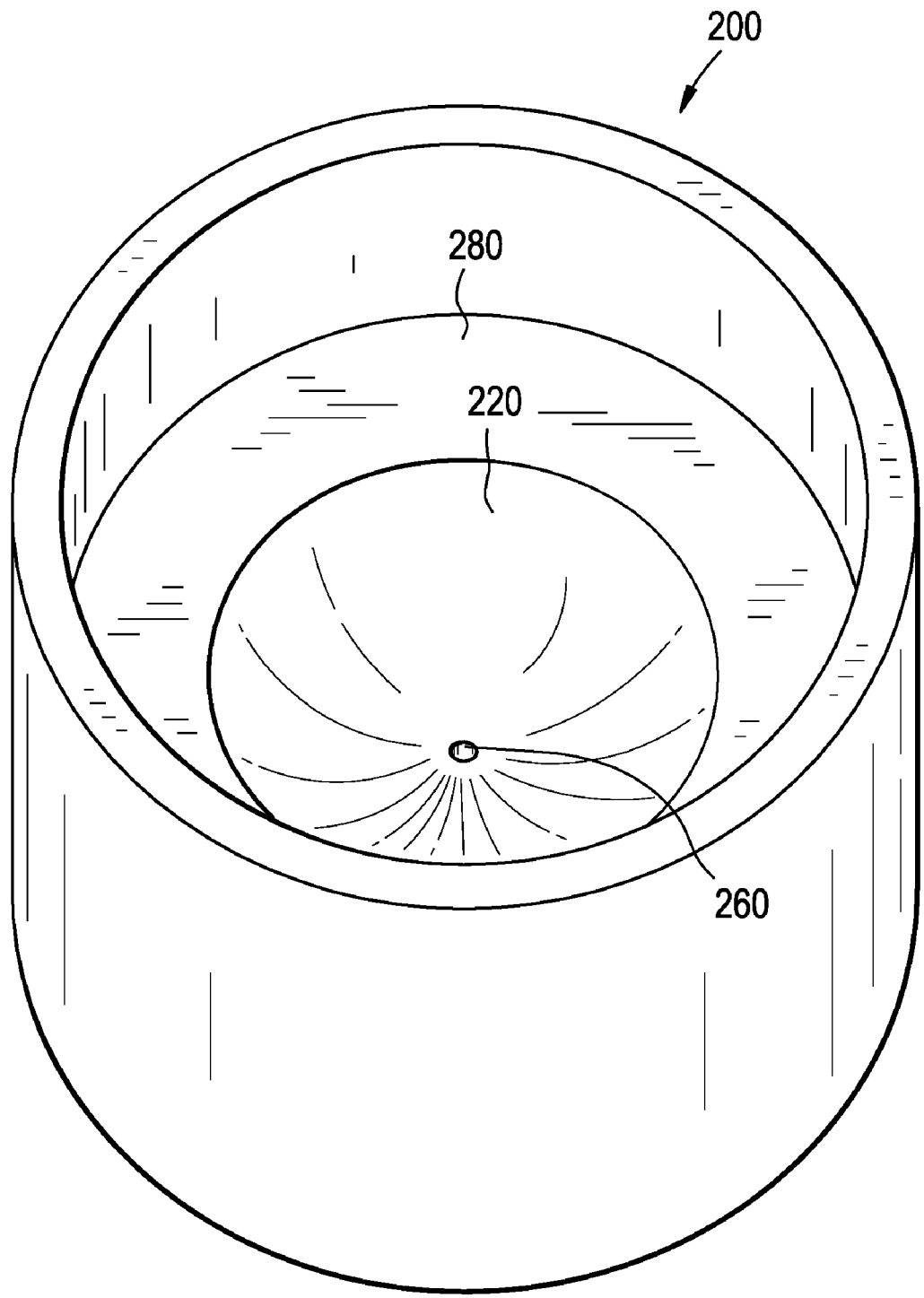
FIG. 2 illustrates a perspective drawing of a female mold.
Figure 3:
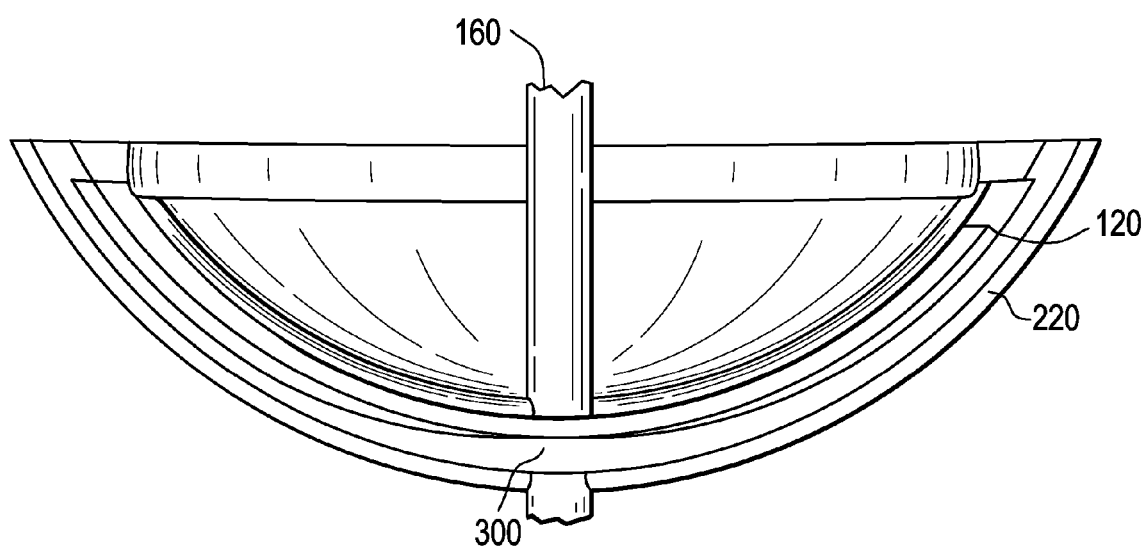
FIG. 3 illustrates a close up cross-sectional drawing of the mated apparatus.

FIG. 1, a perspective drawing of a male mold 100, contains convex testing surface 120, aperture 160, and, male seating ridge 180. FIG. 2, a perspective drawing of a female mold 200, contains concave testing surface 220, aperture 260, and female seating ridge 280. FIG. 3, a close up cross section of mated apparatus, where the mated convex testing surface 120 and concave testing surface 220, define the testing area 300 between those surfaces. Preferably the convex and concave testing surfaces are of a size and shape to mimic the shape of the eye and an eyelid. Testing area 300 is large enough to hold an ophthalmic lens (not shown) and a volume of solution. It is preferred that the testing area be sized to house an ophthalmic lens and about 50 μL to about 500 μL of solution, more preferably, about 100 μL to about 400 μL of solution, most preferably about 200 μL of solution.

The convex or concave testing surfaces of the apparatus may contain grooves that provide pathways for the small volumes of solutions to pass over the surfaces of ophthalmic lenses contained in the testing area. These grooves may be in any number or orientation, but preferably a convex or concave testing surface contains at least one latitudinal groove and one radial groove. It is preferred that such grooves intersect at a point on the convex or concave testing surface. In an embodiment of the invention is illustrated in the following figures both the concave and the convex surfaces contain radial and latitudinal grooves.

Figure 4:
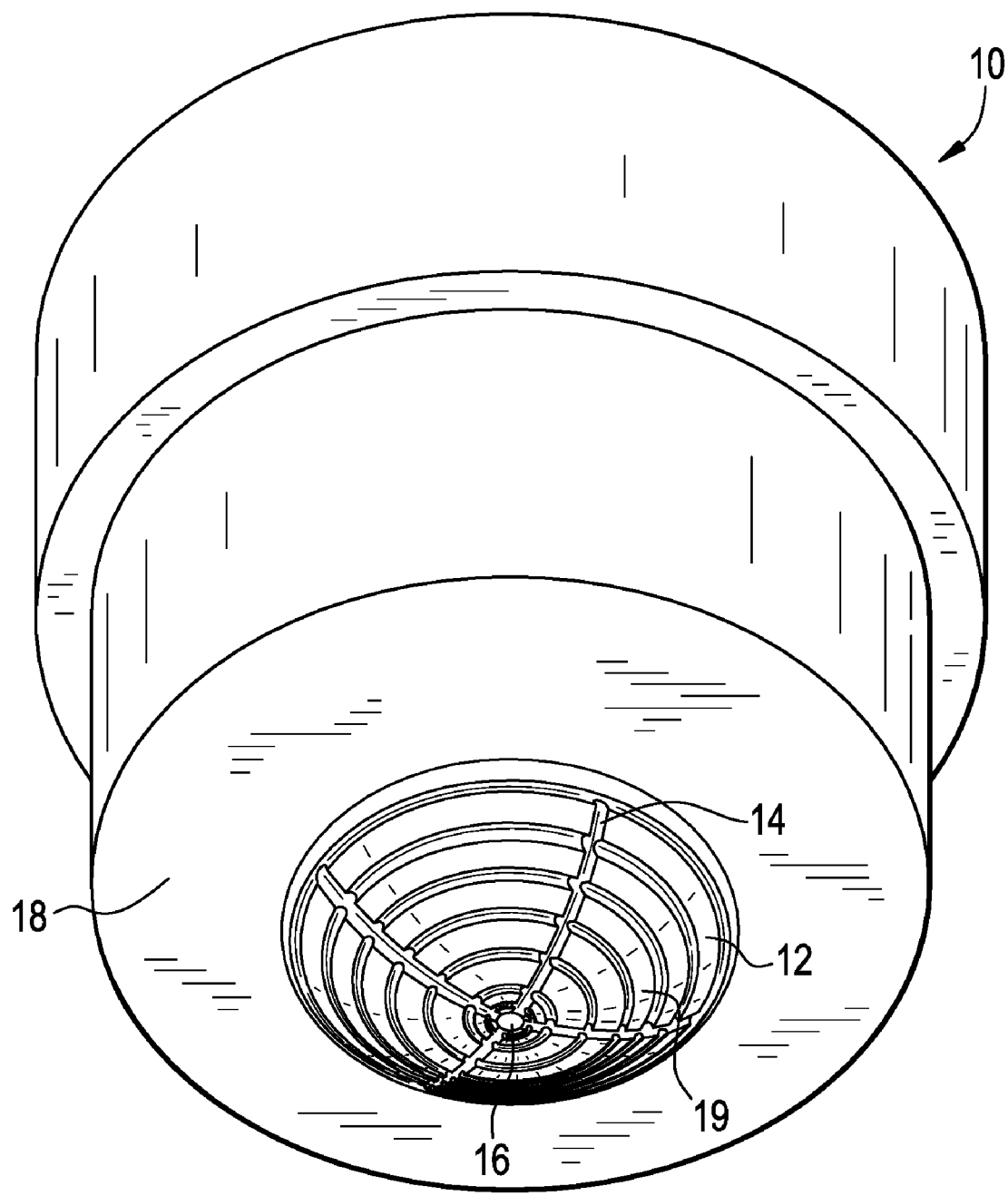
FIG. 4 illustrates a perspective drawing of a male mold.
Figure 5:
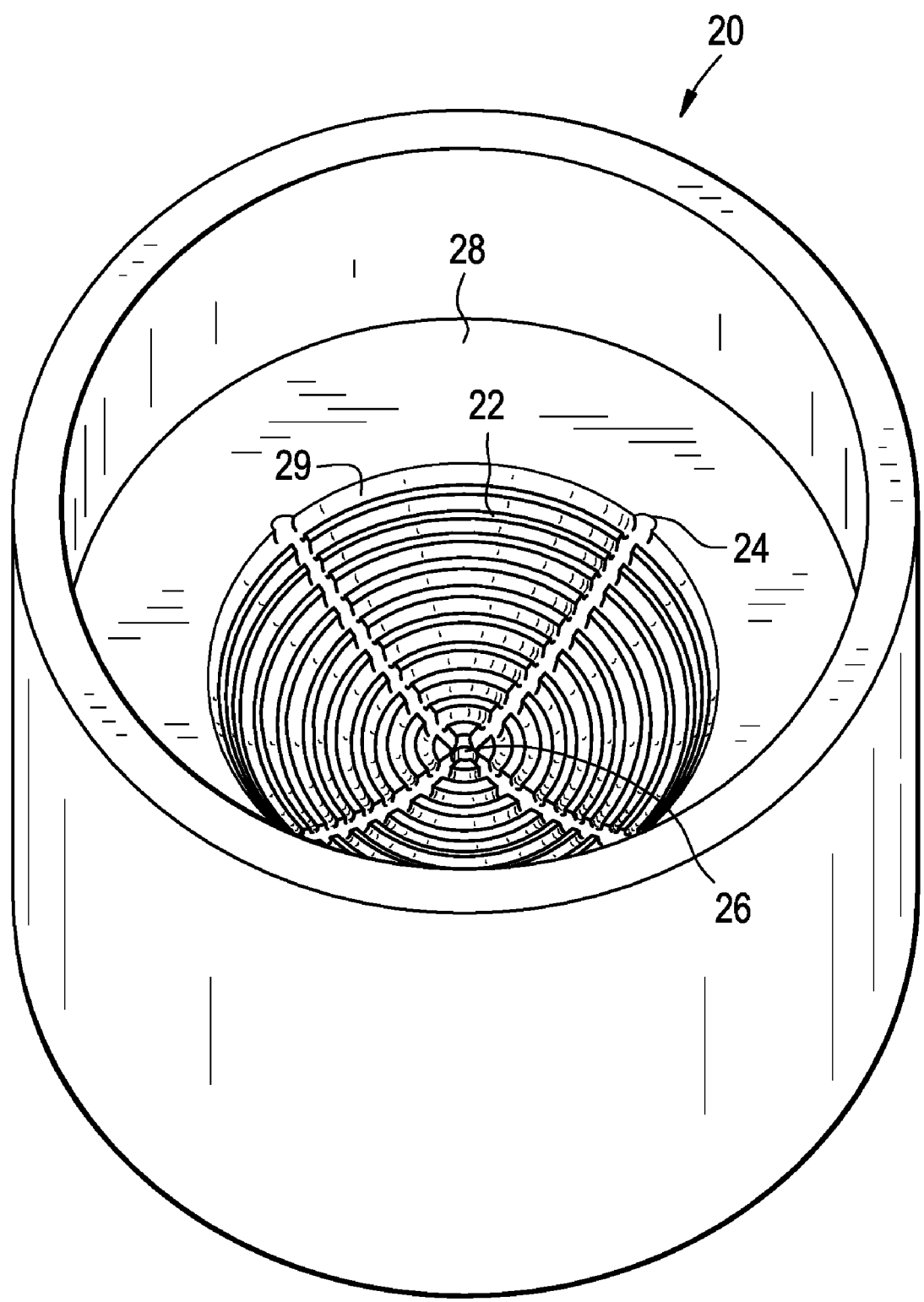
FIG. 5 illustrates a perspective drawing of a female mold.

FIG. 4, a perspective drawing of a male mold 10, contains convex testing surface 12, four radial grooves 14, aperture 16, male seating ridge 18, and six concentric latitudinal grooves 19. FIG. 5, a perspective drawing of a female mold 20, contains concave testing surface 22, four radial grooves, 24, aperture 26, female seating ridge 28, and nine concentric latitudinal grooves 29. The radial grooves on the convex testing surface intersect with the latitudinal grooves so as to allow solutions that flow through the apertures, to more easily flow to the entire convex testing surface. This structural arrangement exists on the concave testing surface as well. Each testing surface may contain the same or different numbers of radial grooves. It is preferred that each testing surface contain contains at least two radial grooves, more preferably three radial grooves, most preferably four radial grooves. With respect to latitudinal grooves, the number of these grooves on each testing surface may be the same or different. It is preferred that each testing surface contain contains at least four latitudinal grooves, more preferably at least five latitudinal grooves, most preferably at least eight latitudinal grooves. The outer male and female surfaces may be the same or different shapes. In one embodiment of the invention (not illustrated) the outer male surface is concave and the outer female surface is convex. Preferably, the convex and concave testing surfaces are of a size and shape to mimics the shape of an eye and an eyelid.

Figure 6:
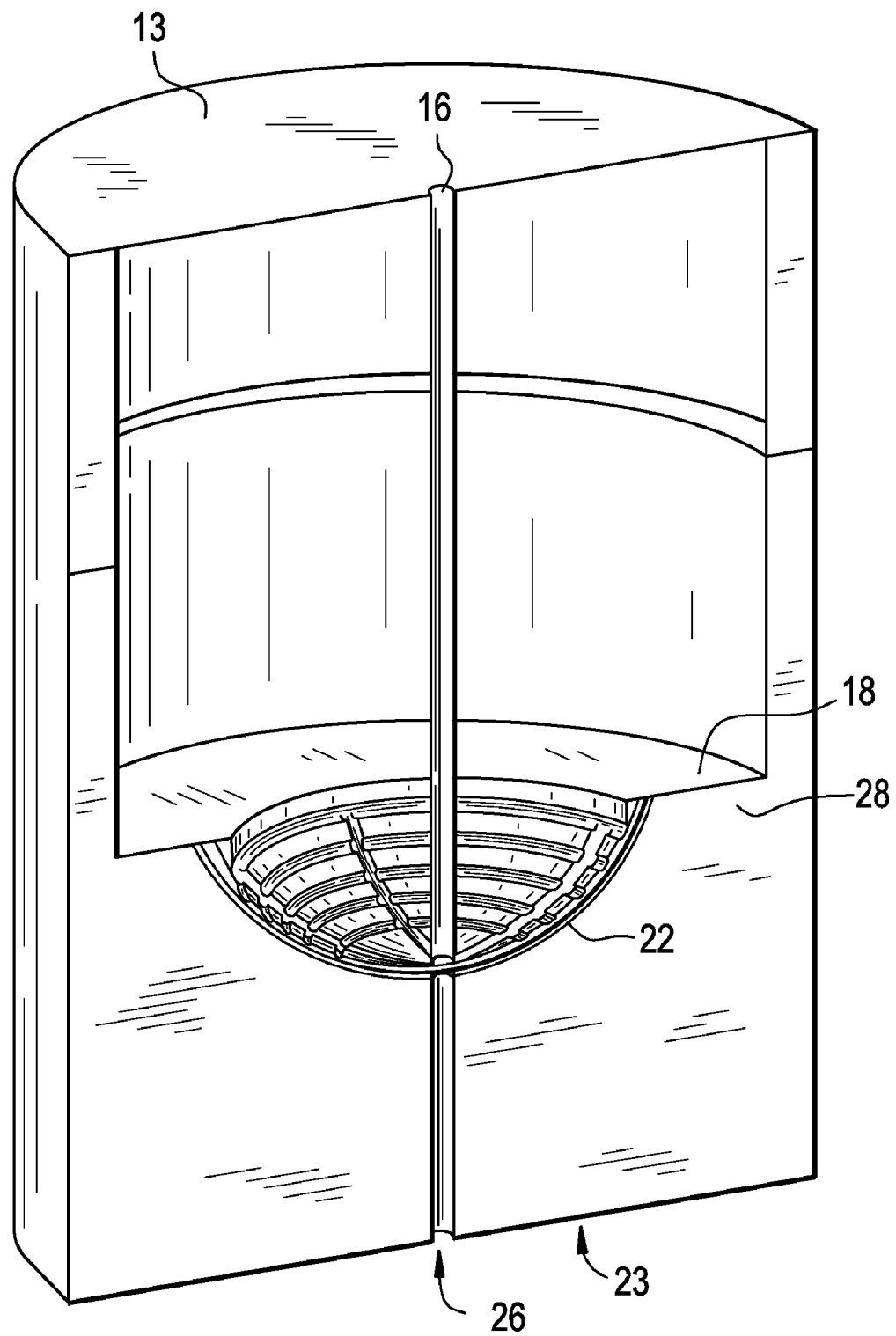
FIG. 6 illustrates a cross-sectional drawing of the mated apparatus.
Figure 7:
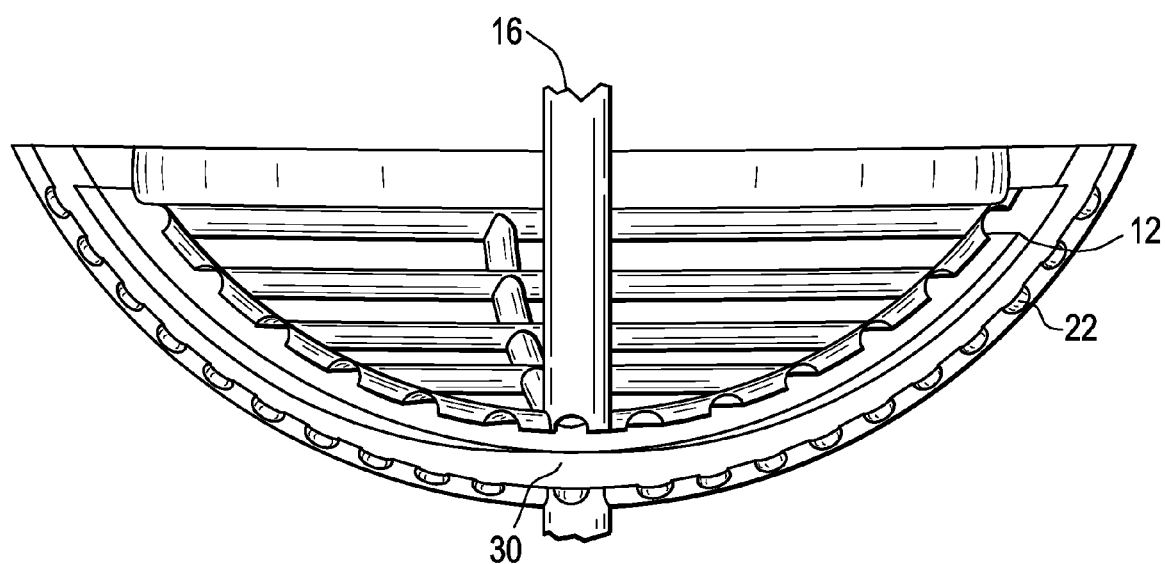
FIG. 7 illustrates a close up cross-sectional drawing of the mated apparatus.

FIG. 6, a cross section of the mated apparatus, with male mold 10, female mold 20, male outer surface 13, female outer surface 23, male seating ridge 18, and female seating ridge 28. As illustrated in FIG. 6, aperture 16 extends from male outer surface 13 to the convex testing surface 12 to the testing area not shown. Further, aperture 26 extends from concave testing surface 22 to outer female surface 23. FIG. 7, a close up cross section of mated apparatus, where the mated convex testing surface 12 and concave testing surface 22, define the testing area 30 those surfaces. Testing area 30 is large enough to hold an ophthalmic lens (not shown) and a volume of solution. It is preferred that the testing area be sized to house an ophthalmic lens and about 50 μL to about 500 μL of solution, more preferably, about 100 μL to about 400 μL of solution, most preferably about 200 μL of solution.

The apparatus of the invention may be prepared from durable thermoplastic materials, such as thermoplastic resins, polyolefins, and thermoplastic polyesters. Examples of such materials include but are not limited to low medium, medium and high density polypropylene, polyethylene and co-polymers thereof, poly-4-methylpentene, fluorinated ethylene propylene copolymers, ethylene fluoroethylene copolymers, polyacetal resins, polacrylether, polyarylether sulfones, nylons, and the like. The apparatus may be prepared by injection molding thermoforming and the like.

Further the invention includes a method of testing the diffusion rate of an ophthalmic device comprising a pharmaceutical agent, wherein the method comprises the steps of
(a) placing an ophthalmic lens comprising a pharmaceutical agent in the testing area of an apparatus comprising a male mold and a female mold,
wherein said male mold comprises a convex testing surface an outer male surface, male seating ridge extending from the perimeter of the convex testing surface, and an aperture extending from said outer male surface to said convex testing surface,
wherein said female mold comprises an outer female surface a concave testing surface, female seating ridge extending from the perimeter of the concave testing surface, and an aperture extending from said concave testing surface to said outer female surface,
wherein when the male mold and the female mold are mated, the male seating ridge sits on the female seating ridge and creates a testing area between the male convex testing surface and the female concave testing surface.
(b) adding a solution to the aperture of the male mold from the outer male surface, and
(c) monitoring the solution that emerges from the aperture of the outer female surface to determine the presence or absence of the pharmaceutical agent.

As used herein the term male mold, female mold, radial groove, latitudinal groove, testing area convex testing surface, and concave testing surface are as described above.

As used herein, "pharmaceutical agents refers to pharmaceutical or nutraceutical compounds used to treat conditions of the eye, and such compound degrade in the presence of oxygen and certain transition metals. Examples of pharmaceutical compounds include antihistamines, antibiotics, antibacterial agents, antiviral agents, antifungal agents, analgesics, anesthetics, antiallergeneic agents, mast cell stabilizers, steroidal and non-steroidal anti-inflammatory agents, angiogenesis inhibitors; antimetabolites, fibrinolytics, neuroprotective drugs, angiostatic steroids, mydriatics, cyclopegic mydriatics; miotics; vasoconstrictors; vasodilators, anticlotting agents; anticancer agents, antisense agents, immunomodulatory agents, carbonic anhydrase inhibitors, integrin antabonistsl; cyclooxygenase inhibitors, VEGF antagonists; immunosuppressant agents and the like. Particularly, examples of pharmaceutical compounds include but are not limited to acrivastine, antazoline, astemizole, azatadine, azelastine, buclizine, bupivacaine, cetirizine, clemastine, cyclizine, cyproheptadine, ebastine, emedastine, ephedrine, eucatropine, fexofenadine, homatropine, hydroxyzine, ketotifen, levocabastine, levoceterizine, lomefloxacin, meclizine, mepivacaine, mequitazine, methdilazine, methapyrilene, mianserin, naphazoline norastemizole, norebastine, ofloxacin, oxymetazoline, pheniramine, phenylephrine, physostigmine, picumast, promethazine, scopolamine, terfenadine, tetrahydrozoline, thiethylperazine, timolol, trimeprazine, triprolidine, pharmaceutically acceptable salts and mixtures thereof. Preferred pharmaceutical compounds include acrivatine, antazoline, astemizole, azatadine, azelastine, clemastine, cyproheptadine, ebastine, emedastine, eucatropine, fexofenadine, homatropine, hydroxyzine, ketotife, levocabastine, levoceterizine, meclizine, mequitazine, methdialazine, methapyrilene, norastemizole, norebastine, oxymetazoline, physootigmine, picumast, promethazine, scopolamine, terfenadine, tetrahyerozoline, fimilol, trimeprazine, triprolidine, and pharmaceutically acceptable salts thereof. Particularly preferred pharmaceutical compounds include phenarimine, ketotifen, ketotifen fumarate nor ketotifen fumarate, 11-dihydro-11-(1-methyl-4-piperidinylidene)-5H-imidazo[2,1-b][3]benzazepine-3-carboxaldehyde (CAS# 147084-10-4), olapatadine and mixtures thereof. More particularly preferred pharmaceutical compounds include ketotifen fumarate, 11-dihydro-11-(1-methyl-4-piperidinylidene)-5H-imidazo[2,1-b][3]benzazepine-3-carboxaldehyde (CAS# 147084-10-4) and mixtures thereof.

Examples of nutraceutical compounds include vitamins and supplements such as vitamins A, D, E, lutein, zeaxanthin, lipoic acid, flavonoids, ophthalmicially compatible fatty acids, such as omega 3 and omega 6 fatty acids, combinations thereof, combinations with pharmaceutical compounds and the like. The methods of the invention may be used to detect the discharge rate (or uptake rate) of ophthalmic lenses containing about 8 μg or more of pharmaceutical agent. Preferably, the discharge rate for ophthalmic lenses that contain about 8 μg to about 90 μg, more preferably about 10 μg to about 40 μg, more preferably about 10 μg to about 25 μg may be determined by the methods of this invention.

As used herein, "ophthalmic lens" refers to a device that resides in or on the eye. These devices can provide optical correction or may be cosmetic. Ophthalmic lenses include but are not limited to soft contact lenses, intraocular lenses, overlay lenses, ocular inserts, and optical inserts. The preferred lenses of the invention are soft contact lenses made from silicone elastomers or hydrogels, which include but are not limited to silicone hydrogels, and fluorohydrogels. Soft contact lens formulations are disclosed in U.S. Pat. No. 5,710, 302, WO 9421698, EP 406161, JP 2000016905, U.S. Pat. Nos. 5,998,498, 6,087,415, 5,760,100, 5,776,9995,789,461, 5,849,811, and 5,965,631. The foregoing references are hereby incorporated by reference in their entirety. The particularly preferred ophthalmic lenses of the inventions are known by the United States Approved Names of acofilcon A, alofilcon A, alphafilcon A, amifilcon A, astifilcon A, atalafilcon A, balafilcon A, bisfilcon A, bufilcon A, comfilcon, crofilcon A, cyclofilcon A, darfilcon A, deltafilcon A, deltafilcon B, dimefilcon A, drooxifilcon A, epsifilcon A, esterifilcon A, etafilcon A, focofilcon A, genfilcon A, govafilcon A, hefilcon A, hefilcon B, hefilcon D, hilafilcon A, hilafilcon B, hioxifilcon B, hioxifilcon C, hixoifilcon A, hydrofilcon A, lenefilcon A, licryfilcon A, licryfilcon B, lidofilcon A, lidofilcon B, lotrafilcon A, lotrafilcon B, mafilcon A, mesifilcon A, methafilcon B, mipafilcon A, nelfilcon A, netrafilcon A, ocufilcon A, ocufilcon B, ocufilcon C, ocufilcon D, ocufilcon E, ofilcon A, omafilcon A, oxyfilcon A, pentafilcon A, perfilcon A, pevafilcon A, phemfilcon A, polymacon, silafilcon A, siloxyfilcon A, tefilcon A, tetrafilcon A, trifilcon A, vifilcon, and xylofilcon A. More particularly preferred ophthalmic lenses of the invention are genfilcon A, lenefilcon A, comfilcon, lotrafilcon A, lotrafilcon B, and balafilcon A. The most preferred lenses include etafilcon A, nelfilcon A, hilafilcon, vifilcon, and polymacon.

The "solutions" that are used in methods of this invention may be water-based solutions. Solutions that mimic natural tear film are preferred. Typical solutions include, without limitation, saline solutions, other buffered solutions, and deionized water. The preferred aqueous solution is deionized water or saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof.

As used herein "monitoring" refers to methods of analyzing the solution to determine the concentration of pharmaceutical agent in the solution. Examples of such detecting methods include but are not limited to HPLC, UV Spectormeters and the like.

Still further the invention includes, a method of measuring the uptake rate of a pharmaceutical agent to an ophthalmic lens, wherein the method comprises the steps of
(a) placing an ophthalmic lens in the testing area of an apparatus comprising a male mold and a female mold,
  wherein said male mold comprises a convex testing surface an outer male surface, male seating ridge extending from the perimeter of the convex testing surface, and an aperture extending from said outer male surface to said convex testing surface,
  wherein said female mold comprises an outer female surface a concave testing surface, female seating ridge extending from the perimeter of the concave testing surface, and an aperture extending from said concave testing surface to said outer female surface,
  wherein when the male mold and the female mold are mated, the male seating ridge sits on the female seating ridge and creates a testing area between the male convex testing surface and the female concave testing surface.
(b) adding a solution comprising a pharmaceutical agent to the aperture of the male mold from the outer male surface, and
(c) monitoring the solution that emerges from the aperture of the outer female surface to determine the presence or absence of the pharmaceutical agent.

As used herein the term male mold, female mold, radial groove, latitudinal groove, testing area convex testing surface, concave testing surface, pharmaceutical agent, ophthalmic lens, solution and monitoring are as described above.

There are other circumstances when one would desire to test the performance of an ophthalmic lens in an ocular environment, other than when said ophthalmic lens contains a pharmaceutical agent. For example if one wanted to determine whether surfactants, excipients, preservatives, wetting agents or other components of solutions ("eyecare solution components") were absorbed by the lens, it would be useful to have a test that mimics the performance of the lens in an ocular environment. In light of this need this invention includes a method of measuring the uptake rate of an eyecare solution component to an ophthalmic lens, wherein the method comprises the steps of
(a) placing an ophthalmic lens in the testing area of an apparatus comprising a male mold and a female mold,
  wherein said male mold comprises a convex testing surface an outer male surface, male seating ridge extending from the perimeter of the convex testing surface, and an aperture extending from said outer male surface to said convex testing surface,
  wherein said female mold comprises an outer female surface a concave testing surface, female seating ridge extending from the perimeter of the concave testing surface, and an aperture extending from said concave testing surface to said outer female surface,
  wherein when the male mold and the female mold are mated, the male seating ridge sits on the female seating ridge and creates a testing area between the male convex testing surface and the female concave testing surface.
(b) adding a solution comprising eyecare solution components to the aperture of the male mold from the outer male surface, and
(c) monitoring the solution that emerges from the aperture of the outer female surface to determine the presence or absence of the eyecare solution component.

As used herein the term male mold, female mold, radial groove, latitudinal groove, testing area convex testing surface, concave testing surface, eyecare solution component, ophthalmic lens, solution and monitoring are as described above.

The specific embodiments of the apparatuses and methods of the invention illustrate, but do not limit the invention. They are meant only to suggest a method of practicing the invention. Those knowledgeable in contact lenses as well as other specialties may find other methods of practicing the invention. However, those methods are deemed to be within the scope of this invention.

What is claimed is:
1. A method of testing the diffusion rate of an ophthalmic device comprising a pharmaceutical agent, wherein the method comprises the steps of
(a) placing an ophthalmic lens comprising a pharmaceutical agent in the testing area of an apparatus comprising a male mold and a female mold,
  wherein said male mold comprises a convex testing surface an outer male surface, male seating ridge extending from the perimeter of the convex testing surface, and an aperture extending from said outer male surface to said convex testing surface,
  wherein said female mold comprises an outer female surface a concave testing surface, female seating ridge extending from the perimeter of the concave testing surface, and an aperture extending from said concave testing surface to said outer female surface,
  wherein when the male mold and the female mold are mated, the male seating ridge sits on the female seating ridge and creates a testing area between the male convex testing surface and the female concave testing surface.
(b) adding a solution to the aperture of the male mold from the outer male surface, and
(c) monitoring the solution that emerges from the aperture of the outer female surface to determine the presence or absence of the pharmaceutical agent wherein said convex testing surface comprises at least one radial groove extending from the aperture to the perimeter of the convex testing surface and at least one latitudinal groove that intersects the at least one radial groove.

2. The method of claim 1 wherein the ophthalmic lens is selected from the group consisting of acofilcon A, alofilcon A, alphafilcon A, amifilcon A, astifilcon A, atalafilcon A, balafilcon A, bisfilcon A, bufilcon A, comfilcon, crofilcon A, cyclofilcon A, darfilcon A, deltafilcon A, deltafilcon B, dimefilcon A, drooxifilcon A, epsifilcon A, esterifilcon A, etafilcon A, focofilcon A, genfilcon A, govafilcon A, hefilcon A, hefilcon B, hefilcon D, hilafilcon A, hilafilcon B, hioxifilcon B, hioxifilcon C, hixoifilcon A, hydrofilcon A, lenefilcon A, licryfilcon A, licryfilcon B, lidofilcon A, lidofilcon B, lotrafilcon A, lotrafilcon B, mafilcon A, mesifilcon A, methafilcon B, mipafilcon A, nelfilcon A, netrafilcon A, ocufilcon A, ocufilcon B, ocufilcon C, ocufilcon D, ocufilcon E, ofilcon A, omafilcon A, oxyfilcon A, pentafilcon A, perfilcon A, pevafilcon A, phemfilcon A, polymacon, silafilcon A, siloxyfilcon A, tefilcon A, tetrafilcon A, trifilcon A, vifilcon, and xylofilcon A.

3. The method of claim 1 wherein said concave testing surface comprises at least one radial groove extending from the aperture to the perimeter of the concave testing surface and at least one latitudinal groove that intersects the at least one radial groove.

4. The method of claim 1 wherein the convex testing surface comprises at least two radial grooves and at least three latitudinal grooves and the concave surface comprises at least two radial grooves and at least three latitudinal grooves.

5. A method of measuring the uptake rate of a pharmaceutical agent to an ophthalmic lens, wherein the method comprises the steps of
(a) placing an ophthalmic lens in the testing area of an apparatus comprising a male mold and a female mold,
wherein said male mold comprises a convex testing surface an outer male surface, male seating ridge extending from the perimeter of the convex testing surface, and an aperture extending from said outer male surface to said convex testing surface,
wherein said female mold comprises an outer female surface a concave testing surface, female seating ridge extending from the perimeter of the concave testing surface, and an aperture extending from said concave testing surface to said outer female surface,
wherein when the male mold and the female mold are mated, the male seating ridge sits on the female seating ridge and creates a testing area between the male convex testing surface and the female concave testing surface.
(b) adding a solution comprising a pharmaceutical agent to the aperture of the male mold from the outer male surface, and
(c) monitoring the solution that emerges from the aperture of the outer female surface to determine the presence or absence of the pharmaceutical agent
wherein said convex testing surface comprises at least one radial groove extending from the aperture to the perimeter of the convex testing surface and at least one latitudinal groove that intersects the at least one radial groove.

6. The method of claim 5 wherein the ophthalmic lens is selected from the group consisting of acofilcon A, alofilcon A, alphafilcon A, amifilcon A, astifilcon A, atalafilcon A, balafilcon A, bisfilcon A, bufilcon A, comfilcon, crofilcon A, cyclofilcon A, darfilcon A, deltafilcon A, deltafilcon B, dimefilcon A, drooxifilcon A, epsifilcon A, esterifilcon A, etafilcon A, focofilcon A, genfilcon A, govafilcon A, hefilcon A, hefilcon B, hefilcon D, hilafilcon A, hilafilcon B, hioxifilcon B, hioxifilcon C, hixoifilcon A, hydrofilcon A, lenefilcon A, licryfilcon A, licryfilcon B, lidofilcon A, lidofilcon B, lotrafilcon A, lotrafilcon B, mafilcon A, mesifilcon A, methafilcon B, mipafilcon A, nelfilcon A, netrafilcon A, ocufilcon A, ocufilcon B, ocufilcon C, ocufilcon D, ocufilcon E, ofilcon A, omafilcon A, oxyfilcon A, pentafilcon A, perfilcon A, pevafilcon A, phemfilcon A, polymacon, silafilcon A, siloxyfilcon A, tefilcon A, tetrafilcon A, trifilcon A, vifilcon, and xylofilcon A.

7. The method of claim 5 wherein said concave testing surface comprises at least one radial groove extending from the aperture to the perimeter of the concave testing surface and at least one latitudinal groove that intersects the at least one radial groove.

8. The method of claim 7 wherein the convex testing surface comprises at least two radial grooves and at least three latitudinal grooves and the concave surface comprises at least two radial grooves and at least three latitudinal grooves.

9. A method of measuring the uptake rate of an eyecare solution component to an ophthalmic lens, wherein the method comprises the steps of
(a) placing an ophthalmic lens in the testing area of an apparatus comprising a male mold and a female mold,
wherein said male mold comprises a convex testing surface an outer male surface, male seating ridge extending from the perimeter of the convex testing surface, and an aperture extending from said outer male surface to said convex testing surface,
wherein said female mold comprises an outer female surface a concave testing surface, female seating ridge extending from the perimeter of the concave testing surface, and an aperture extending from said concave testing surface to said outer female surface,
wherein when the male mold and the female mold are mated, the male seating ridge sits on the female seating ridge and creates a testing area between the male convex testing surface and the female concave testing surface,
(b) adding a solution comprising eyecare solution components to the aperture of the male mold from the outer male surface, and
(c) monitoring the solution that emerges from the aperture of the outer female surface to determine the presence or absence of the eyecare solution component,
wherein said convex testing surface comprises at least one radial groove extending from the aperture to the perimeter of the convex testing surface and at least one latitudinal groove that intersects the at least one radial groove.

10. The method of claims 9 wherein said concave testing surface comprises at least one radial groove extending from the aperture to the perimeter of the concave testing surface and at least one latitudinal groove that intersects the at least one radial groove.

* * * * *